(12) United States Patent
Rozenberg

(10) Patent No.: US 8,241,576 B2
(45) Date of Patent: Aug. 14, 2012

(54) MICROBIAL INACTIVATION BY MULTIPLE PRESSURE SPIKES DELIVERED WITH REGULATED FREQUENCY

(75) Inventor: Oleg Rozenberg, Brooklyn, NY (US)

(73) Assignee: Oleg Rozenberg, Brooklyn, NY (US)

( * ) Notice: Subject to any disclaimer, the term of this patent is extended or adjusted under 35 U.S.C. 154(b) by 943 days.

(21) Appl. No.: 11/827,956

(22) Filed: Jul. 13, 2007

(65) Prior Publication Data

US 2009/0016937 A1 Jan. 15, 2009

(51) Int. Cl.
*B06B 1/00* (2006.01)
*A61L 2/00* (2006.01)
(52) U.S. Cl. .......................... 422/127; 422/128; 422/39
(58) Field of Classification Search .................. 422/39, 422/127, 128; 366/267, 333
See application file for complete search history.

(56) References Cited

U.S. PATENT DOCUMENTS

| | | | | |
|---|---|---|---|---|
| 4,187,762 A | * | 2/1980 | Buzby | 91/37 |
| 4,480,654 A | * | 11/1984 | Firey | 137/119.09 |
| 5,190,373 A | * | 3/1993 | Dickson et al. | 366/146 |
| 5,316,745 A | * | 5/1994 | Ting et al. | 422/295 |
| 5,996,478 A | * | 12/1999 | Schuman et al. | 99/453 |
| 6,120,732 A | | 9/2000 | Toledo et al. | |
| 6,277,610 B1 | | 8/2001 | Grae | |
| 6,696,019 B2 | * | 2/2004 | Laugharn et al. | 422/39 |
| 2006/0292274 A1 | * | 12/2006 | Garwood | 426/335 |

FOREIGN PATENT DOCUMENTS

JP 06327417 A * 11/1994

OTHER PUBLICATIONS

English Translation of Japanese Document No. JP 06327417 A provided by the Industrial Property Digital Library: Sato, Masanori et al.; Nov. 29, 1994.*

* cited by examiner

*Primary Examiner* — Kevin Joyner

(57) ABSTRACT

A process and apparatus wherein multiple instantaneous pressure pulsations with a regulated frequency and amplitude are applied to various biological substances in order to eliminate the undesired microorganisms in these substances with minimal negative effect on the quality of these substances, and, further, to use these in mass production of foodstuffs pharmaceuticals for treatment of human blood or plasma, and for research to establish a specific frequency of pressure pulsations at which a particular type of bacteria could be selectively destroyed while other components of the substance remain intact.

18 Claims, 15 Drawing Sheets

MICROBIAL INACTIVATION BY MULTIPLE PRESSURE SPIKES DELIVERED WITH REGULATED FREQUENCY

REFERENCE TO RELATED APPLICATION

This application is a non-provisional application of U.S. of co pending Provisional Application conformation No. 7469, filed Jul. 18, 2006 by the same inventor and entitled MICROBIAL INACTIVATION BY MULTIPLE PRESSURE SPIKES DELIVERED WITH REGULATED FREQUENCY.

BACKGROUND OF THE INVENTION

Many different methods are used to inactivate harmful microorganisms in the pharmaceutical industry, food processing, medicine, and biotechnology. One method, most often used for liquid substances, is a method used in conventional thermal processing. In this method, the temperature of the liquid is kept elevated for a period of time, and higher temperatures usually required shorter time duration to produce the necessary results. In the food industry, however, this method has an adverse effect on flavor, vitamin, and protein content of the final product.

In the biotech industry, millions of genetically engineered, protein-producing *E. coli* bacteria are added to a nutrient-rich growth medium for the mass production of therapeutic proteins. After the bacteria synthesize the desired product, they are pumped into a high pressure tank, where they remain for a period of time under extremely high pressure until their cell walls burst open, releasing the contents. In some instances, a successful outcome requires that the process be repeated several times. This method is also used in the production of juices and other food products. The advantage of the high pressure treatment, as compared to the more popular heat treatment, is that this method inactivates the microorganisms with minimal harm to vitamins or flavoring. However, this method has a number of shortcomings, especially in the area of economic feasibility and engineering limitations. Economic feasibility is limited by the high cost of capital investment for the equipment, low productivity, and the high labor cost of batch process. Economic feasibility is further limited by the long process time, 30 minutes to 1 hour, which is required by some applications. Engineering limitations include concerns about the construction of high pressure vessels with a large enough capacity to hold substantial quantities of product.

In another method used to inactivate microorganisms, the liquid substance is first pressurized and then depressurized by transferring the liquid into an area of reduced pressure through one or more constrictions, as shown in U.S. Pat. No. 6,120,732. This method is based on the principle that bacteria cannot withstand sudden pressure change and substantial mechanical friction. However, passage of a substantial quantity of liquid substance through a small orifice with high speed results in overheating of the orifice due to friction, and leads, in liquids such as milk, to the buildup of a hard substance (milk stone) on the tip of the orifice. The formation of such "milk stone" has a negative effect on the process and often can even block the orifice completely. Other problems include limited throughput and the difficulty of maintaining the liquid under high pressure in a vessel, from which a substantial volume of liquid escapes to the low pressure vessel. These problems render this method impractical for the mass production. Finally, since, in the most cases, the percentage of inactivated bacteria is insufficient, additional treatments are often required to achieve acceptable results.

In another method, a special restrictive nozzle is used in place of an orifice. As in the above method, a partial inactivation of the bacteria is achieved by both sudden pressure drop and mechanical friction. In addition, the restrictive nozzle causes the atomization, or break-up, of the liquid substance into tiny particles. The atomized product is then treated with steam vapor. In this treatment, the atomized particles, when coming into contact with vapor, undergo a sudden temperature rise in addition to the sudden pressure drop. The sudden temperature rise further enhances the inactivation of bacteria. In order to keep the maximum temperature of the treated product down, the vapor temperature would need to be no more then 50-60 degrees Celsius. This is achieved by the introduction of vacuum into the system, as shown in the U.S. Pat. No. 6,277,610. This method, however, does not eliminate the "milk stone" problem or the problem of controlling the product temperature after the nozzle. The difference between the temperature of "cold steam" and the temperature of treated substance is often not substantial enough to effectively inactivate the bacteria. To make this process work, the temperature of the steam would have to be raised, which in turn would adversely affect the quality of the final product.

SUMMARY OF THE INVENTION

It is an object of this invention to provide a method for the purpose of killing harmful microorganisms in various substances with minimal negative effects on the overall quality of these substances.

It is another object of this invention to provide a method for the purpose of killing harmful microorganisms in various substances to be used in mass production and to be cost and energy efficient.

It is yet another object of this invention to provide a device that generates instantaneous pressure changes with adjustable amplitudes and frequencies in various substances for the purpose of researching an optimal combination of these parameters in the process of killing harmful microorganisms in these substances.

It is yet another object of this invention to provide a device that generates instantaneous pressure changes with adjustable amplitudes for the purpose of selecting the most economically effective combination of pressure amplitude and time duration needed to decrease the quantity of harmful microorganisms to an acceptable level.

It is another object of this invention to provide a device in which the frequency of the instantaneous pressure changes is adjustable for the purpose of researching frequencies most effective in killing bacteria.

It is yet another object of this invention to provide a device to be used in mass production of foodstuffs or therapeutic medication, in which a specific frequency of pressure vibrations is applied to selectively kill certain type of bacteria.

It is yet another object of this invention to provide an energy efficient method for the use in mass production of foodstuffs and medication. The existing methods require either instantaneous heating or cooling of mass quantities of product, or the forcing of mass quantities of product through small orifices under high pressure. Such processes require massive amounts of energy. The process described in present invention, however, is energy efficient due to the fact that pressure spikes are applied to a substance stored in a closed container without necessitating movement of mass or additional heating or cooling of the substance.

It is well established that extreme conditions, such as high temperature, high pressure, and mechanical friction, facilitate the killing of harmful microorganisms. However, some of these conditions, such as temperature and friction, affect the quality of the product negatively and others, such as high pressure, are too costly for the process to be economically practical for mass production. It is also known that rapid changes in temperature and pressure may be used to facilitate the destruction of harmful microorganisms. Although these methods allow the lowering of process temperature while at the same time preserving the quality of the final product, they are too cumbersome to be effectively controlled and economically feasible. The need to move large quantities of substance through a restrictive nozzle in a short period of time, while at the same time maintaining high pressure in front of the nozzle, renders these methods impractical for mass production. In addition, these methods do not deliver reliable results in killing bacteria and also have a problem with the build-up of hard substance in the orifice of the restrictive nozzle, which blocks the nozzle altogether.

In accordance with an aspect of present invention, a multitude of instantaneous pressure changes (pulsations) is applied to various substances for a period of time for the purpose of inactivating harmful microorganisms. The percentage of killed bacteria will increase with the increase either in the frequency or the amplitude of pressure pulsations. Both of these parameters are easily regulated and controlled in present invention and the most economically effective parameters that would produce the least negative effect on the final product can be easily researched.

Furthermore, the novelty of the present invention is in its ability to apply pulses of pressure to the treated substances with a wide range of different frequencies. Every time the substance is pressurized, the outer membrane of the bacteria cell will contract while the internal pressure of the membrane will rise to equalize the outside pressure. Every time the outside pressure is removed, the internal cell pressure will expand the outer shell. Due to inertia and elasticity, the outer shell will also over-expand slightly beyond its original size. As a result, the internal forces in the outer shell will rise and bring the outer shell back to its original size. Normally, these expansions and contractions of the outer shell occur with a specific "natural" frequency. During regular application of pressure spikes, the bacteria vibrate with the frequency of the applied pressure spikes. When the frequency of pressure spikes coincides with the natural frequency of the bacteria cells, a resonance occurs, which increases the amplitude of cell vibrations with each pressure pulsation until the outer membrane bursts and the bacteria is destroyed. In summary, the application of pressure pulsations with frequencies equal or close to the natural frequency of a particular microorganism accomplishes the selective killing of these microorganisms without negative effect, on the final product.

The invention accordingly is comprised of the features of construction, combination of elements, and arrangements of parts that will be exemplified in the system, device, and article of manufacture hereinafter described, and of which the scope of application is as elucidated hereinafter, as will be indicated in the appended claims. In this regard, numerous alternatives within the scope of the present invention, besides those alternatives, preferred embodiments or modes practicing the invention supra, and those to be elucidated, will occur to those skilled in the art.

Other objects, features and advantages of the invention in its details of construction and arrangements of parts will be seen from the above, from the following description of the preferred embodiment when considered with the drawing and from appended claims. In addition, these and other objects and advantages of the present invention will become evident from the description which follows.

DESCRIPTION OF THE PREFERRED EMBODIMENTS

Figure 1:
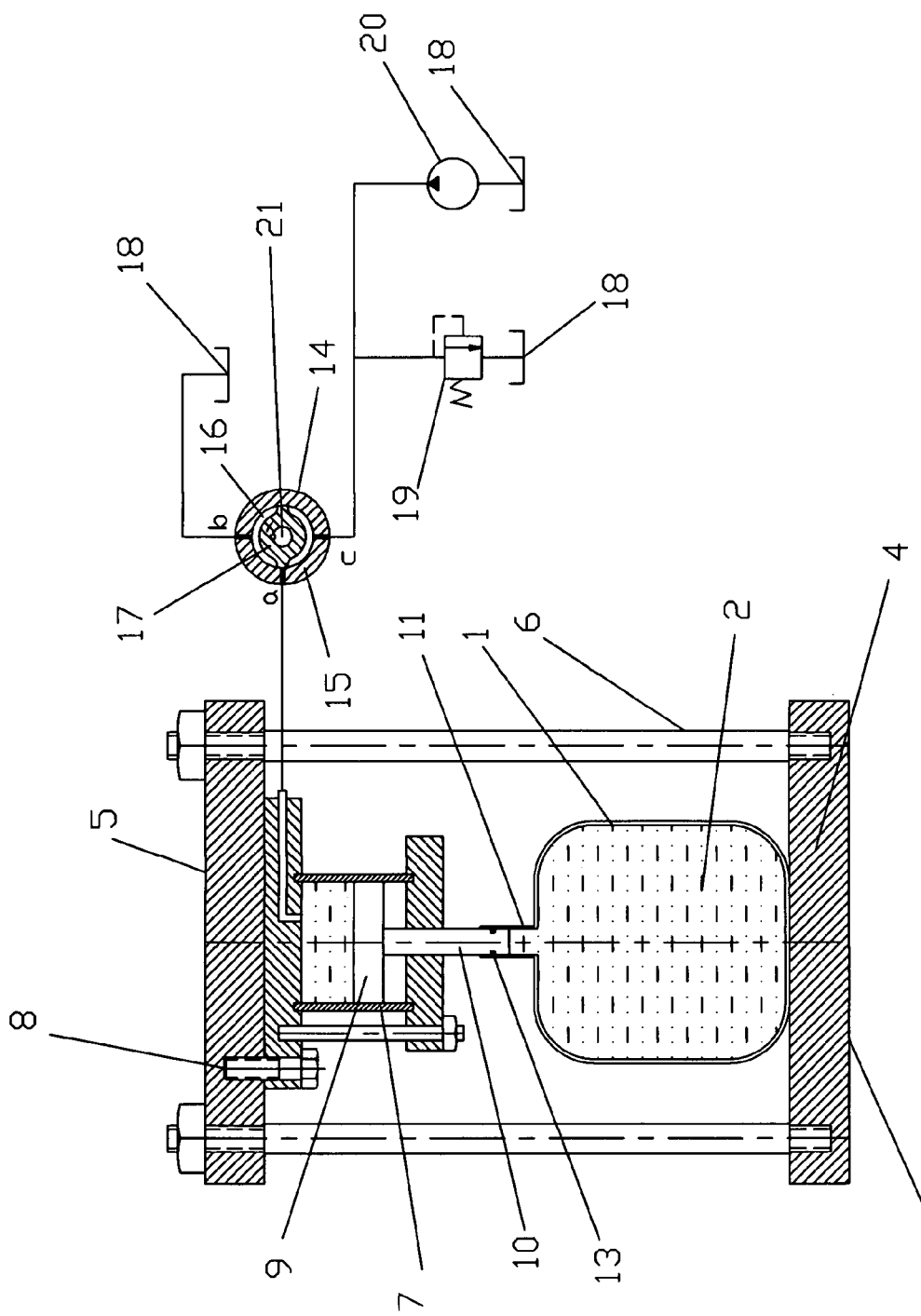
FIG. 1 is a cross-sectional view of a system incorporating present invention where a high pressure hydraulic cylinder with a rotary valve is employed to deliver intermittent high pressure spikes with a regulated frequency to the liquid substance contained in the vessel for the purpose of killing harmful microorganisms in the substance.

With reference to FIG. 1, there is generally shown a cross sectional view of a system incorporating present invention. Vessel 1, containing substance under treatment 2, is placed on bottom plate 4 of stand 3. Stand 3 consists of plates 4 and 5 connected by columns 6. Columns 6 are formed to support the load induced by cylinder 7. Cylinder 7 is mounted to the top plate 5 by bolts 8. The cylinder's piston rod 10 is inserted into neck 11 of vessel 1. High pressure seal 13 is formed at the end of piston rod 10. Piston rod 10 is in contact with the treated substance 2. The volume above piston 9 in cylinder 7 is filled with oil and is connected to rotary valve 14. Rotary valve 14 consists of valve housing 15 and rotor 17. Rotor 17 is formed with two sealed chambers 16. Rotor 17 is connected through axle 21 to a motor with an adjustable speed rotation. Three openings, "a", "b", and "c", are formed in valve housing 15. Opening "a" is connected to the piston side of cylinder 7. Opening "b" is connected to tank 18, while opening "c", through pressure-regulating valve 19, is connected to high pressure pump 20. During the rotation of rotor 17, chambers 16 periodically connect the piston area of cylinder 7 to either low pressure tank port "b" or high pressure port "c", thus intermittently changing the pressure on the piston side of cylinder 7. The oil pressure is regulated by pressure-regulating valve 19. The pressure applied to the substance depends on the diameter of cylinder 7 and the diameter of piston rod 10. Because piston rod 10 is always in contact with substance 2, high pressure in substance 2 is generated instantly. By changing the rotating speed of rotor 17, one can easily control the frequency of the pressure spikes delivered to substance 2 inside vessel 1.

Figure 2:
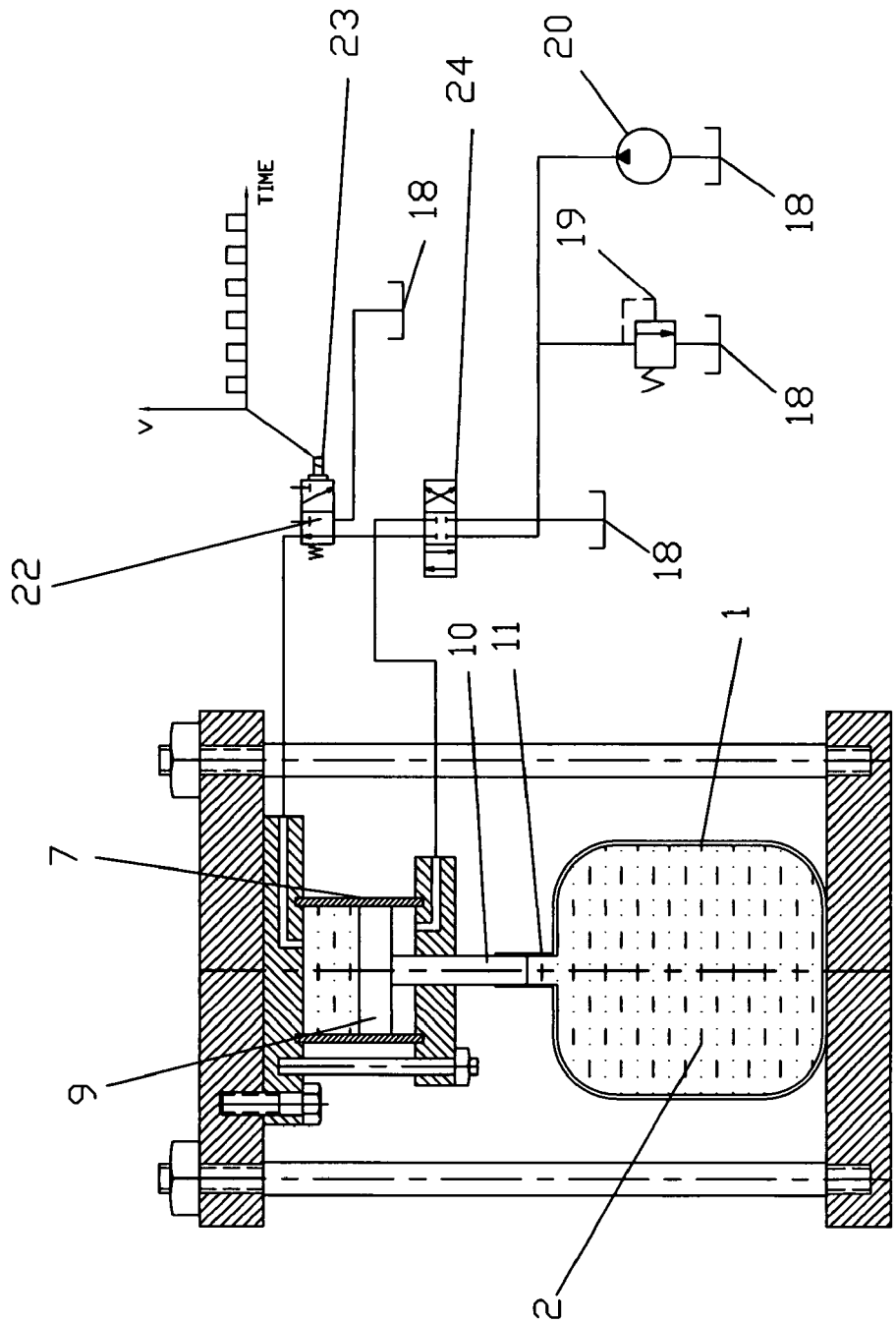
FIG. 2 is a cross-sectional view of a system incorporating present invention where a high pressure hydraulic cylinder controlled by a directional control valve is employed to deliver intermittent high pressure spikes to the liquid substance contained in the vessel for the purpose of killing bacteria in the substance, and, where a three-way directional control valve is used to facilitate the movement of the cylinder's piston rod in and out of the vessel.

With reference to FIG. 2, there is generally shown a cross section of another system, incorporating present invention. In this system, however, the rotating valve is replaced by directional control valve 22 with controlling solenoid 23. Depending on its position, valve 22 connects the volume above piston 9 either to the pressure port or to the tank port. Controlling solenoid 23 receives an "on" or "of" signal intermittently, with a controlled frequency, thus delivering pressure pulsations with the same frequency to substance 2 in container 1. Directional control valve 24 is added to facilitate the movement of piston rod 10 in and out of vessel neck 11. When valve 24 shifts to the right, the system pressure reaches the inlet port of valve 22 and when valve 22 is in its right position, piston rod 10 extends into neck 11 of vessel 1. When both valves 24 and 22 shift to the left, piston rod 10 retracts from the neck 11.

Figure 3:
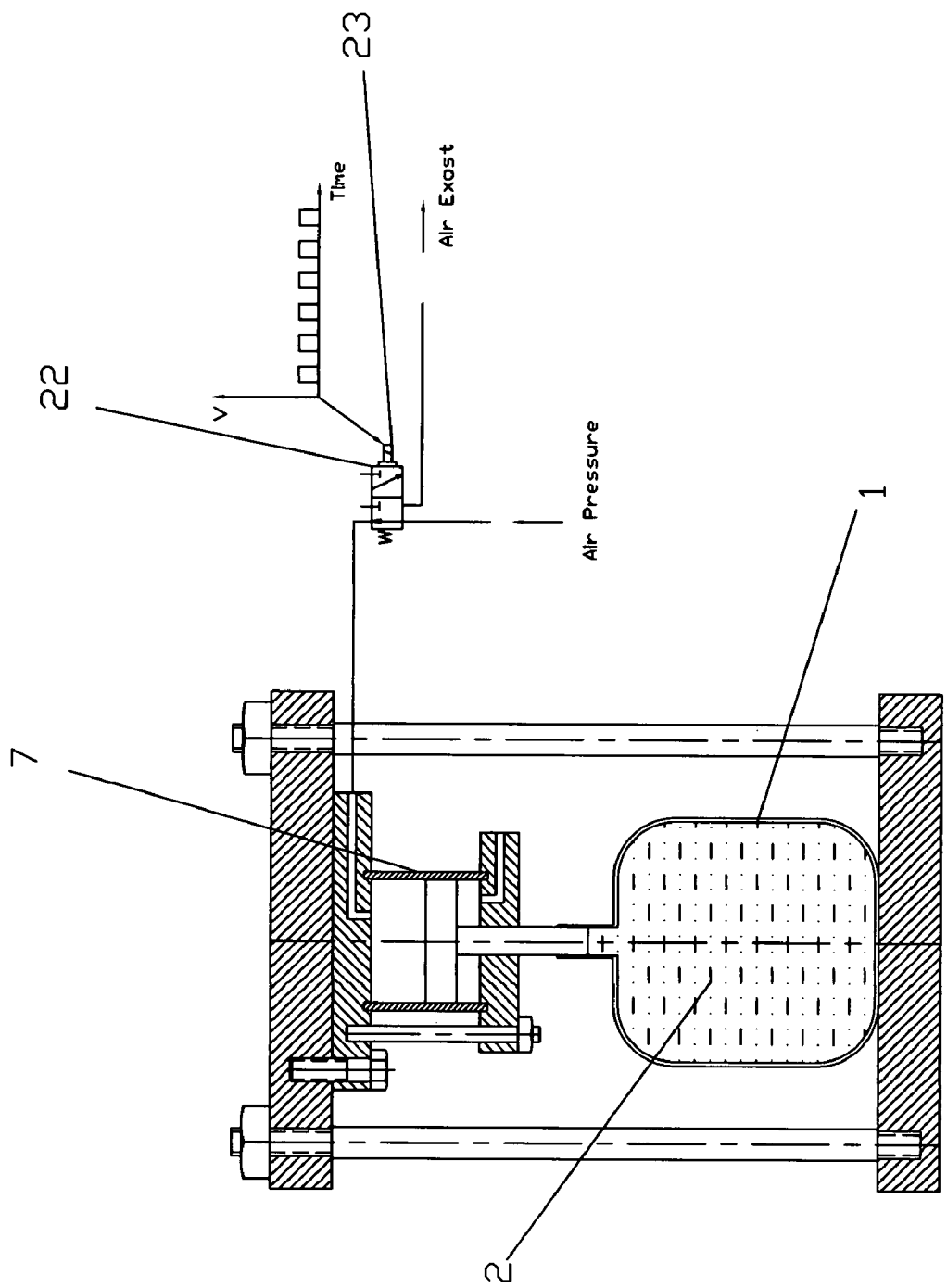
FIG. 3 is a cross-sectional view of present invention where air pressure is used in a cylinder to generate multiple pressure spikes for the purpose of killing harmful microorganisms in the liquid substance contained in the vessel.

With reference to FIG. 3, there is generally shown a cross section of another system incorporating present invention. In this system, however, air pressure is incorporated to produce the pulsating pressure spikes in vessel 1 with regulated frequency. Valve 22 is controlled by solenoid 23 as shown in FIG. 2. If the desired result can be achieved using of lower pressure amplitudes, this system will provides a simple and cost effective solution.

Figure 4:
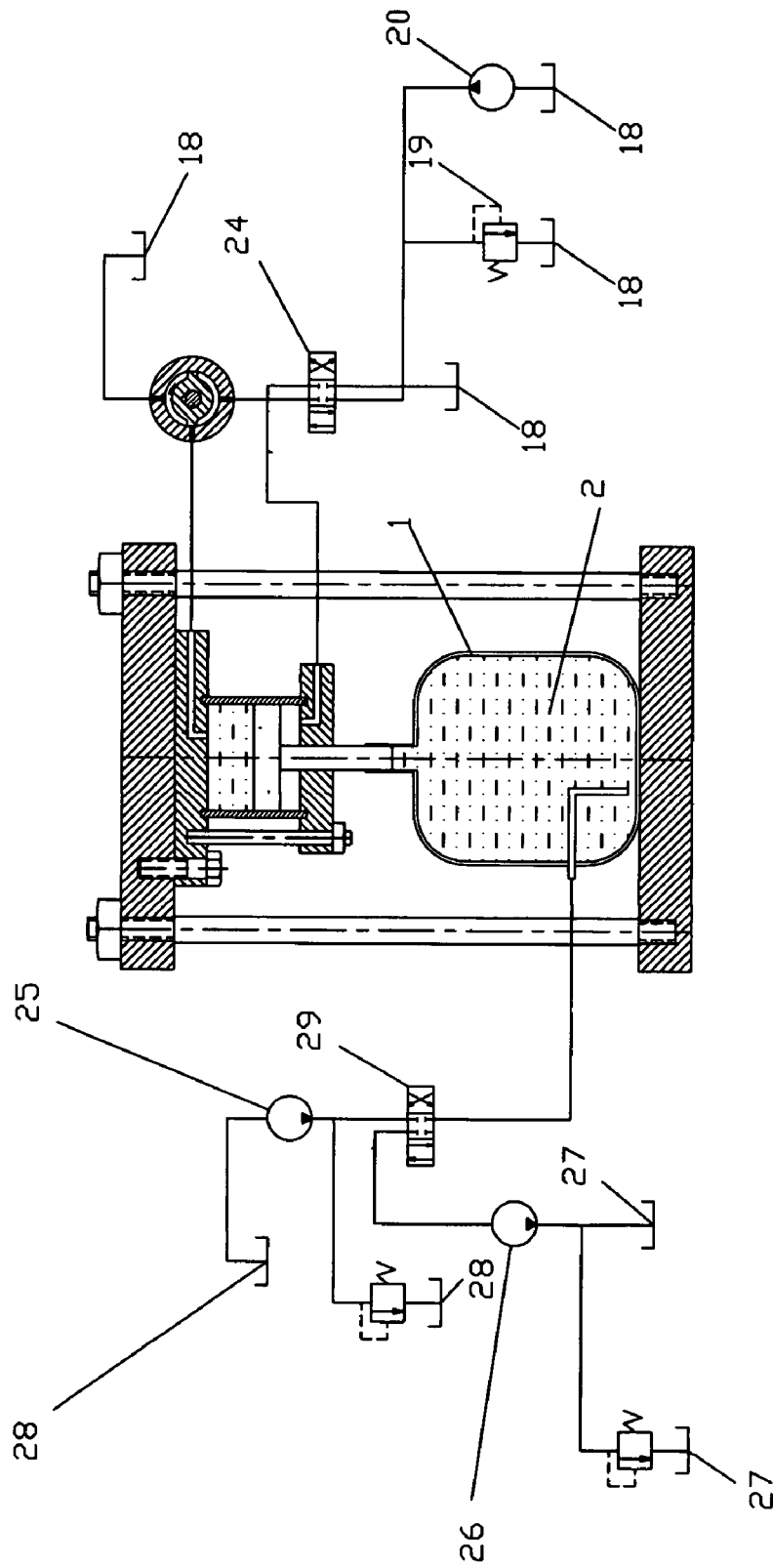
FIG. 4 is a cross-sectional view of a system incorporating present invention where two pumps with pressure-regulating and directional valves are added to automatically load and unload the liquid substance to facilitate continuous manufacturing process.

With reference to FIG. 4, there is generally shown a cross section of another system incorporating present invention. This system is similar to the system in FIG. 1, except that pumps 25 and 26, tanks 27 and 28, and directional control valve 29 is added to provide the automatic loading and unloading of treated product 2. Pump 25 loads the untreated product from tank 28 into vessel 1, while pump 26 unloads the treated product from vessel 1 to tank 27. Directional control valve 29 directs the flow of the product either from tank 28 to vessel 1 or from vessel 1 to tank 27.

Figure 5:
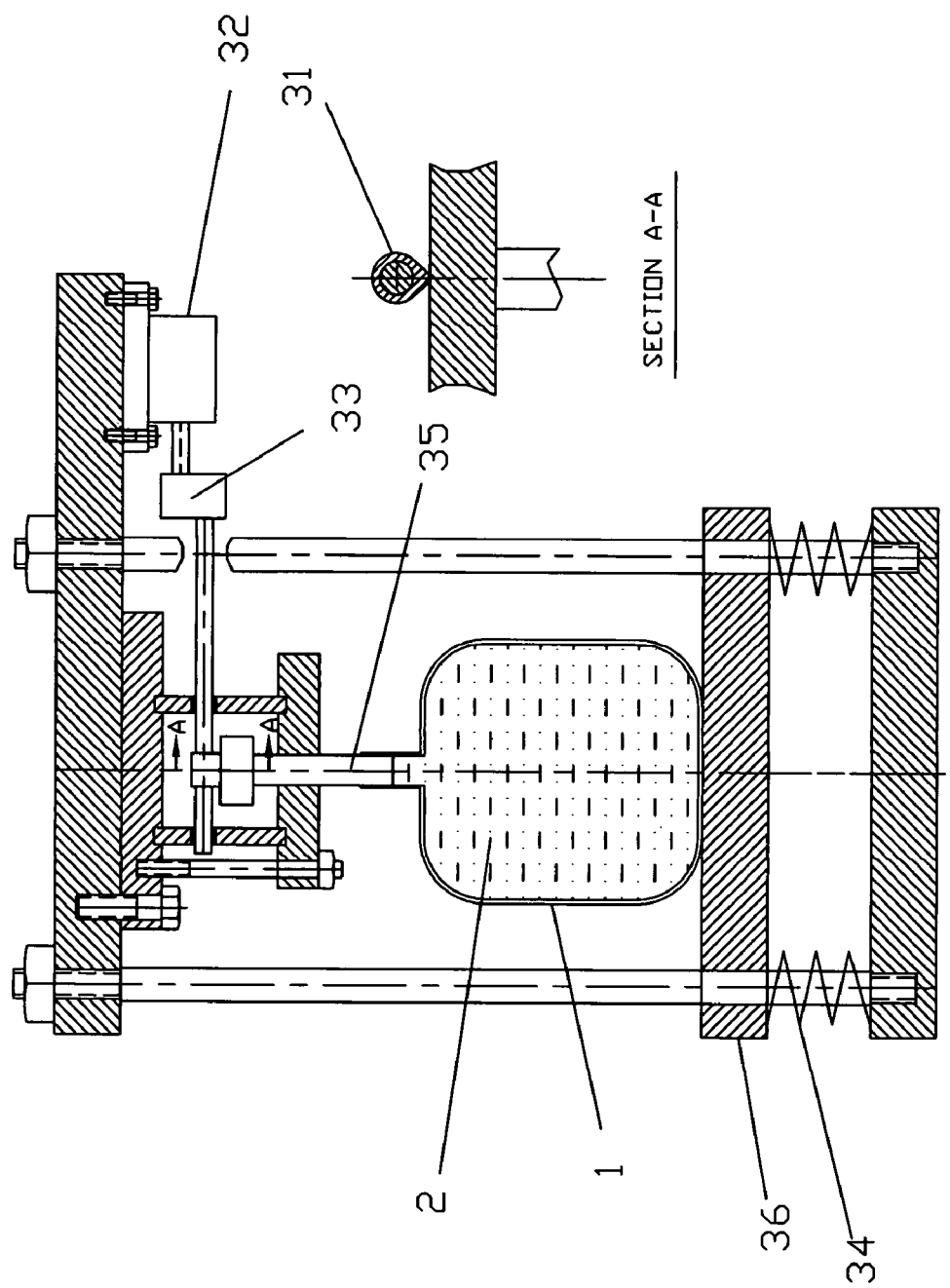
FIG. 5 is a cross-sectional view of a system incorporating present invention where a rotating mechanical cam is incorporated to produce instantaneous pressure pulsations in the liquid substance contained in the vessel.

With reference to FIG. 5, there is generally shown a cross section of another system incorporating present invention. In this system, however, pressure pulsations are produced by rotating cam 31, which is in contact with rod 35. Vessel 1 is placed on spring-loaded platform 36 to prevent rotating cam 31 from breaking. Cam 31 is driven by motor 32 through gear box 33. The frequency of pulsations is regulated either by the speed of motor 32 or by switching gears in gearbox 33. The amplitude of pressure pulsations in this system is regulated either by the stiffness of elastic elements 34 or by the contact area between rod 35 and substance 2.

Figure 6:
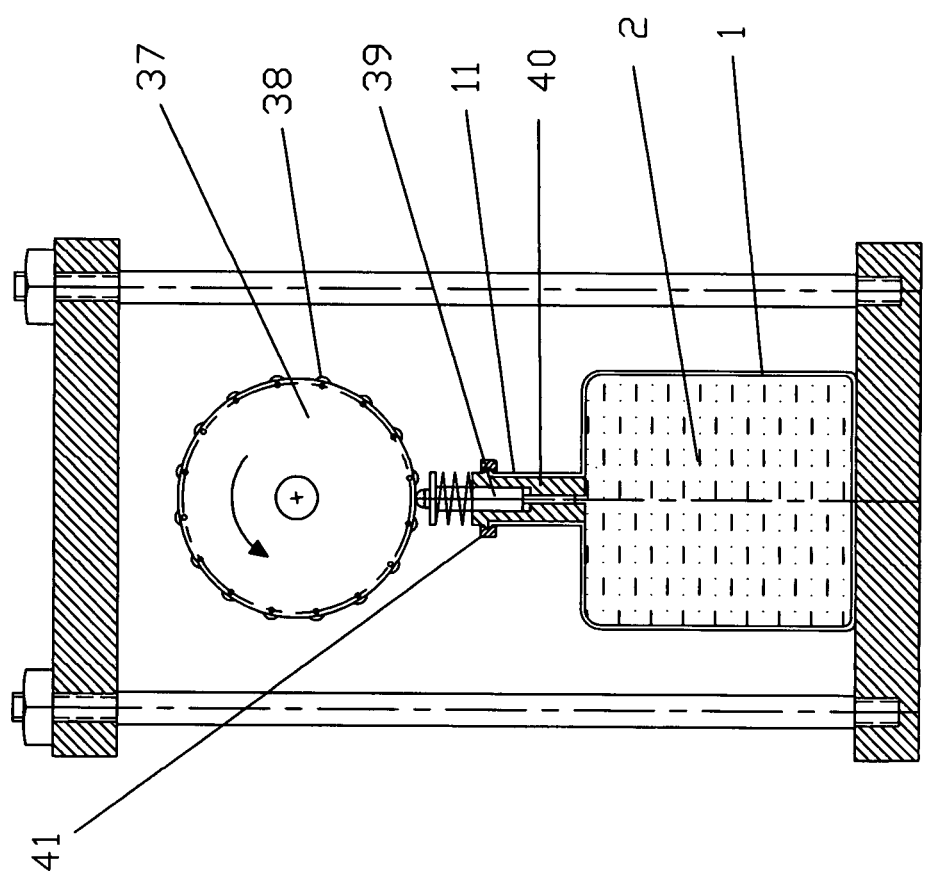
FIG. 6 is a cross-sectional view of present invention where a rotating wheel with a number of actuators, formed on the outer diameter of the wheel, is incorporated to generate high frequency pressure pulsations in the liquid substance contained in the vessel.

With reference to FIG. 6, there is generally shown a cross section of another system incorporating present invention. This system is similar to that of FIG. 5. However, the rotating cam in this system is replaced by a number of rollers 38 formed on the outer diameter of wheel 37. This is done to increase the frequency of pressure pulsations in substance 2. The amplitude of pressure pulsations is controlled by the contact area between push rod 39 and substance 2. To facilitate the use of push rods with different contact areas in one container, insert 40 is formed inside neck 11 and secured by clamp 41. Inserts 40 always have the same outer diameters while the inner diameters are formed to accommodate push rods with different contact areas. By using various insert-push rod combinations, one can regulate the amplitude of pressure pulsations generated in substance 2.

Figure 7:
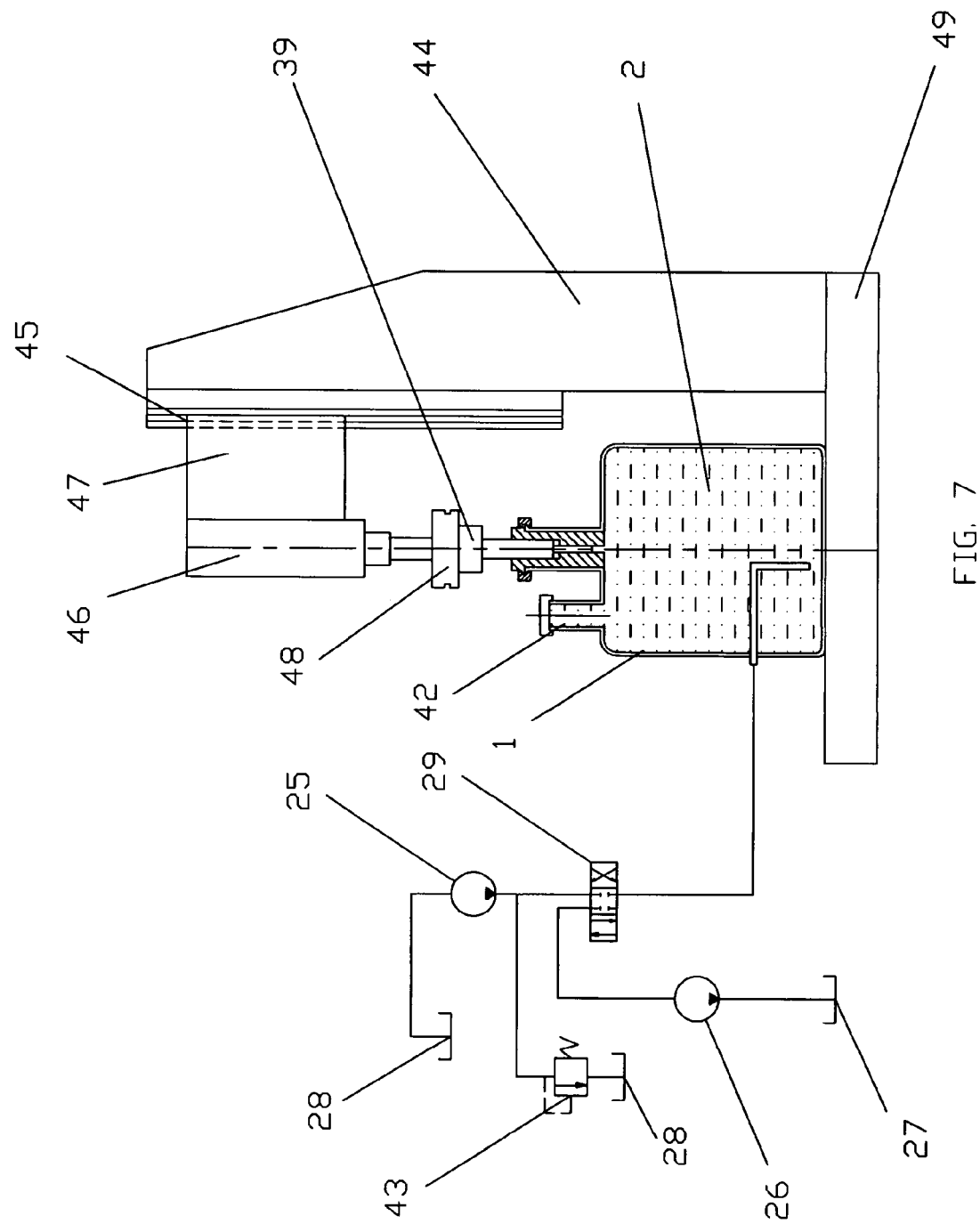
FIG. 7 is a cross-sectional view of present invention where an ultrasonic frequency generator is employed to produce pressure pulsations in liquid substance contained in the vessel.

With reference to FIG. 7, there is generally shown a cross section of another system incorporating present invention. In this system, however, high frequency pressure pulsations are produced by ultrasonic vibrator 47. Ultrasonic vibrators are frequently used for various applications, including ultrasonic welding and the cleaning of metal parts. The frequency and amplitude of vibrations in these devices can be regulated. Ultrasonic device 46 is mounted on rigid column 44, which is mounted on plate 49. Vibrating horn 48 is attached to ultrasonic device 46. The distance between vibrating horn 48 and plate 49 can be adjusted by moving the ultrasonic device 46 up or down on guide rail 45. Once vessel 1 is placed on plate 49, ultrasonic device 46 is brought down until horn 48 is in contact with the top of rod 39, which is in contact with substance 2. The initial pressurization of substance 2 is achieved through pressure regulating valve 43 and pump 25. After the setup is completed, horn 48 starts vibrating, this, in turn, generates pressure pulsations in substance 2 with a frequency equal to the vibration frequency of horn 48. Neck 42 facilitates the removal of trapped air from vessel 2.

Figure 8:
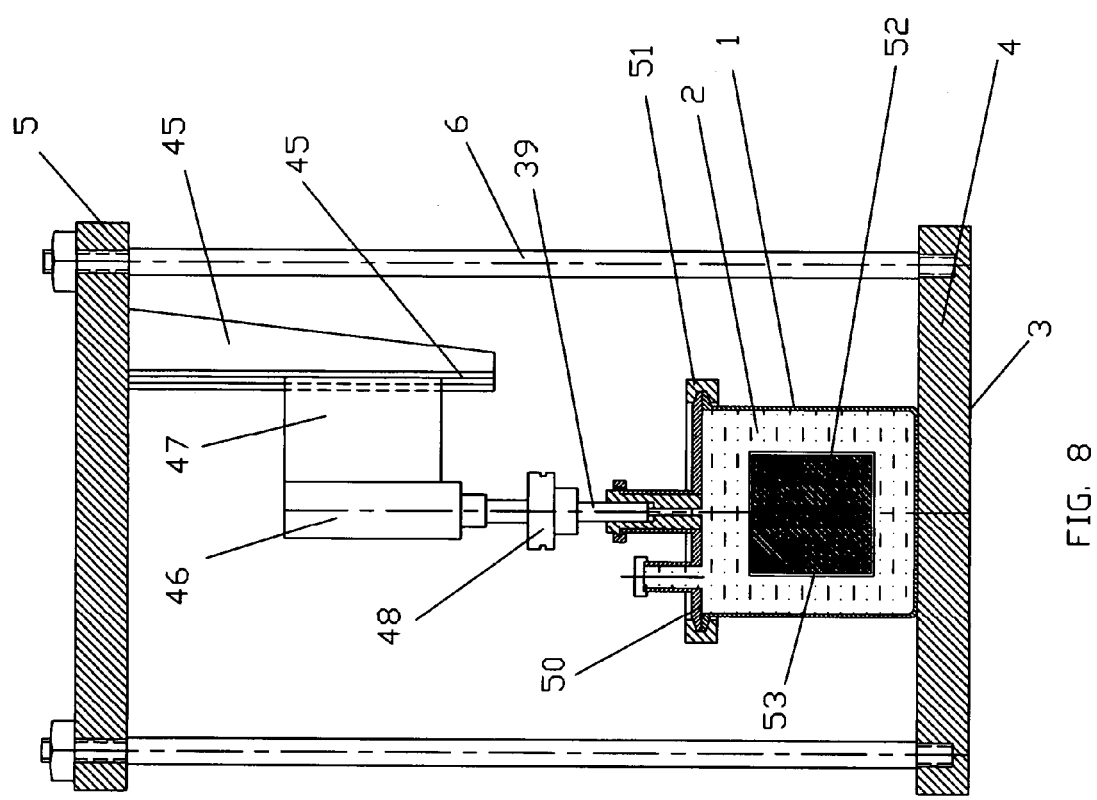
FIG. 8 is a cross-sectional view of present invention, where a solid product, suspended in liquid, is treated to inactivate the harmful microorganisms by instantaneous pressure pulsations.

With reference to FIG. 8, there is generally shown a cross section of another system incorporating present invention. However, this system is formed to be used for the treatment of solid products. Solid product 52 is vacuum-packed in plastic wrap 53 and then placed inside vessel 1. Product 52 is suspended inside vessel 1 and surrounded by liquid 2. Vessel 1 is sealed by cover 50, which is secured to vessel 1 by clamp 51. Ultrasonic device 46 generates pressure pulsations with a set frequency in liquid 2 which are transferred through liquid 2 to product 52. Ultrasonic vibrator 47 is attached to upper plate 5. Due to this setup, the size of vessel 1 is not limited by the size of column 44 and the quantity of substance treated in vessel 1 in one treatment cycle can be increased.

Figure 9:
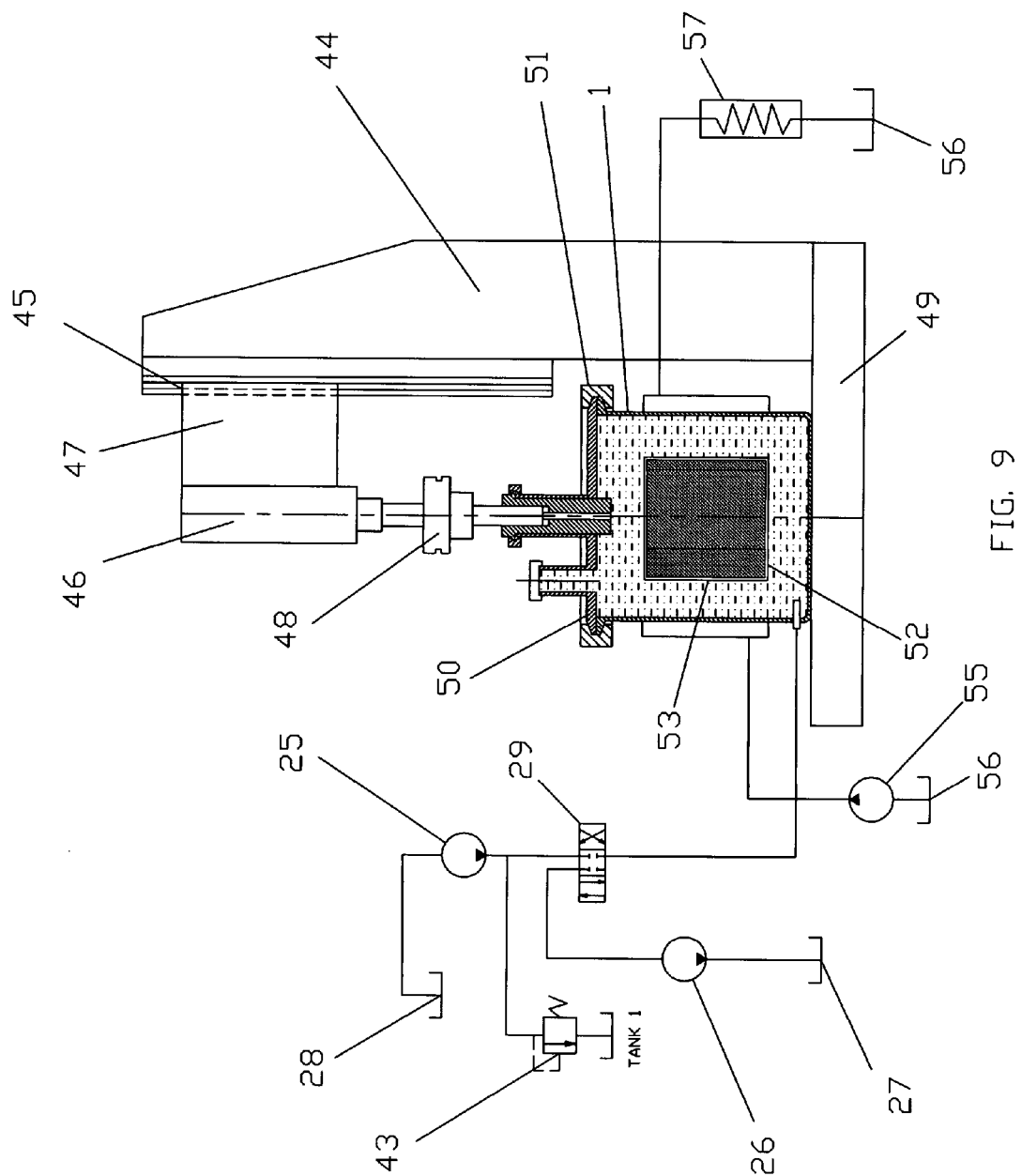
FIG. 9 is a cross-sectional view of present invention, where a cooling jacket is formed around the vessel to facilitate cooling of the liquid substance contained in the vessel during pulsating pressure treatment.

With reference to FIG. 9, there is generally shown a cross section of another system incorporating present invention. In this system, cooling jacket 54 is formed around vessel 1 to control the temperature of substance 2 during the pulsating pressure treatment. A cooling liquid is then pumped from tank 56 by pump 55 through heat exchanger 57 into cooling jacket 54 and back into tank 56.

Figure 10:
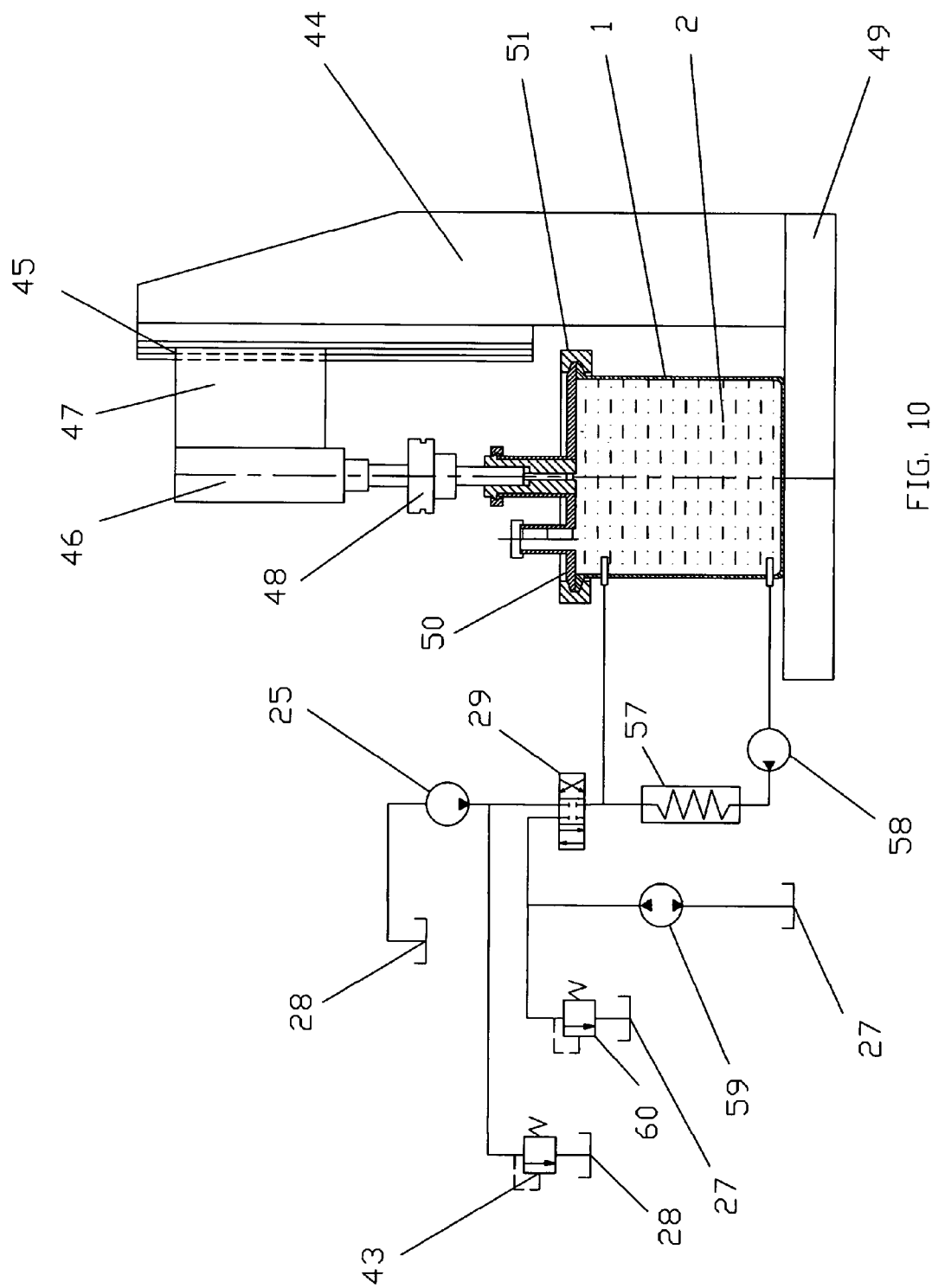
FIG. 10 is a cross-sectional view of present invention, where a heat exchanger is incorporated into the system to facilitate the cooling of the liquid substance contained in the vessel during pulsating pressure treatment.

With reference to FIG. 10, there is generally shown a cross section of another system incorporating present invention. This system is similar to the system described in FIG. 9; however, its cooling arrangement is made to be more efficient. In this system, rather then the cooling jacket controlling the temperature of substance 2, substance 2 itself, is circulated by pump 58 through heat exchanger 57 during or between pressure pulsation treatments.

Figure 11:
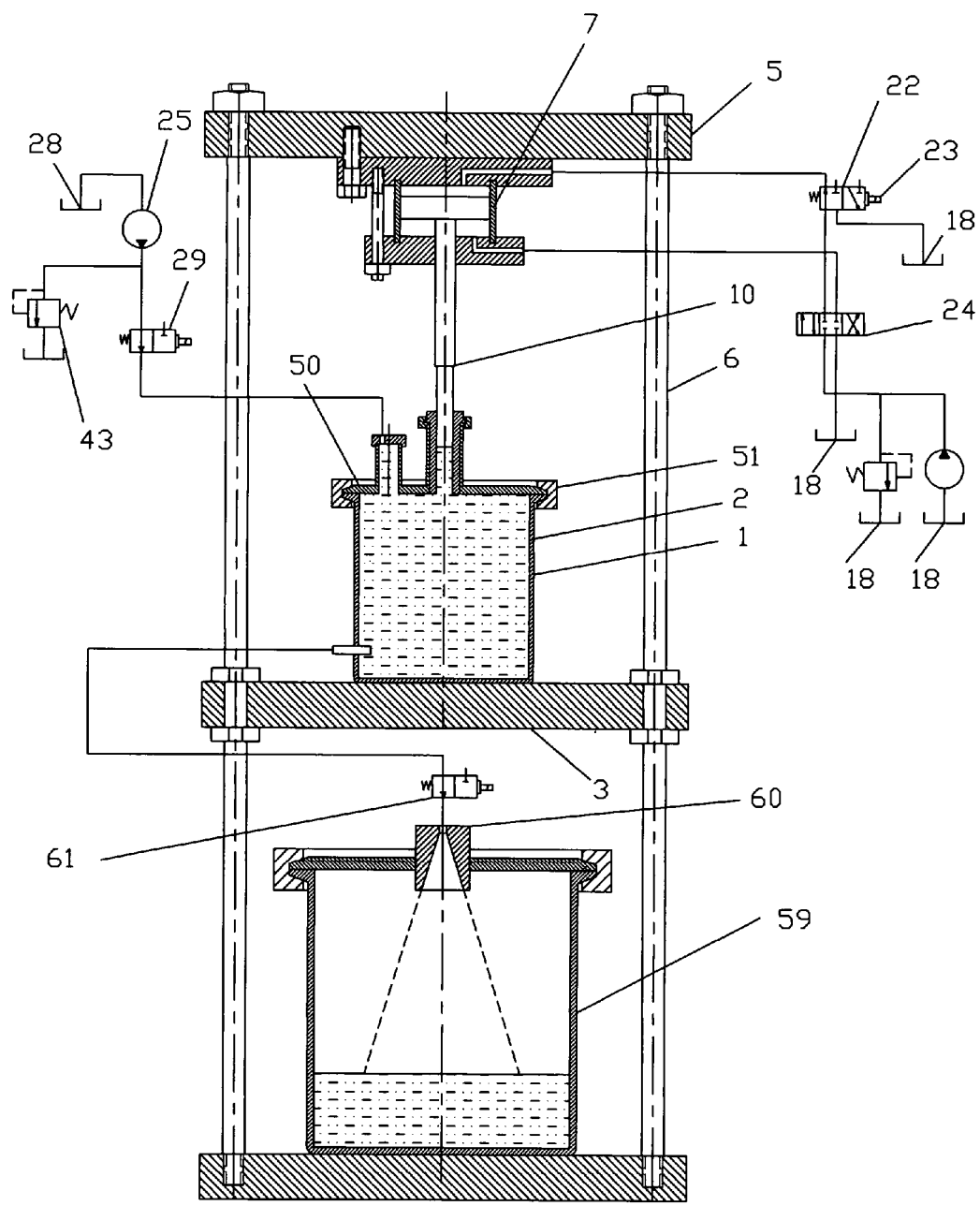
FIG. 11 is a cross-sectional view of present invention, where a cylinder is made to alternate between the generation of pressure pulsations in the substance contained in the high pressure vessel and the pumping of the substance from the first vessel to the second vessel through a restriction.

With reference to FIG. 11, there is generally shown a cross section of another system incorporating present invention. In this system, however, cylinder 7 alternates between producing instantaneous pressure pulsations in substance 2, while the substance is locked between valves 29 and 61, and pumping parts of the substance 2 from container 1 into container 59 through nozzle 60 when valve 61 is open. Initially, control valve 22 works with a set frequency in an oscillating mode that produces pressure pulsations needed to treat substance 2. Thereafter, treatment valve 22 shifts to the right, permitting the free flow of oil under pressure to the piston side of cylinder 7. Valve 61, subsequently, opens after that, permitting the substance to escape from vessel 1 into vessel 2. Valve 24, through which pressure was delivered to valve 22, stays in its rightward position. System pressure, through valves 22 and 24, acts on the piston side of cylinder 7. Piston rod 10 extends, pushing a portion of substance 2 from vessel 1, through valve 61 and nozzle 60, into vessel 59. After piston rod 10 extends fully, valve 61 shifts to block the flow from vessel 1 into vessel 59, and valve 22 shifts to the left, connecting the piston side of cylinder 7 to tank 18. At this moment, valve 29 shifts to the right and the untreated substance moves from storage tank 28 to vessel 1 by pump 25. Under pressure from substance 2, cylinder rod 10 retracts. After cylinder rod 10 retracts fully, valve 29 closes and valve 22 starts oscillating again. In this system, the automatic unloading of vessel 1 is done without additional pumps, and valves and the system can be adapted to combine different types of substance treatments in one smooth process. Each time the treated portion of substance 2 is pushed out from the bottom of vessel 1, an untreated substance is added at the top of vessel 1, with minimal mixing between them. By the time the added substance reaches the bottom of vessel 1 it will have been subjected to a number of high pressure pulsation treatments. Nozzle 60 will provide additional treatment to substance 2 if necessary, and other types of treatments, such as "cold vapor" and vacuum, can also be incorporated inside vessel 2.

Figure 12:
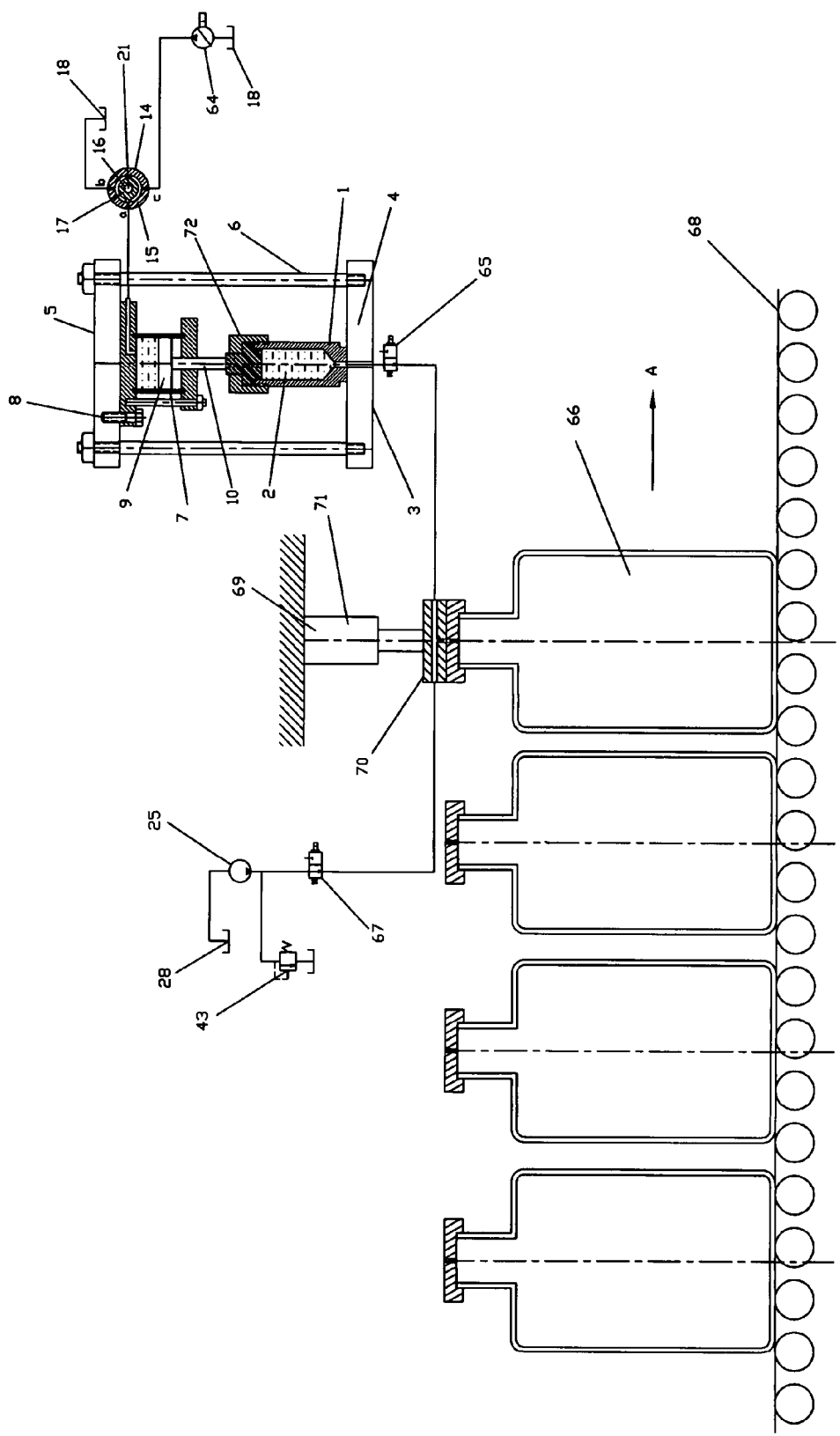
FIG. 12 is a cross-sectional view of present invention to be used in mass production, where one pulsating pressure-generating device is used to treat multiple containers filled with substance, which are moving on a conveyer.

With reference to FIG. 12, there is generally shown a cross sectional view of another system incorporating present invention. In this system, however, a single device generating pressure pulsations is used to consecutively treat multiple containers moving on a conveyor belt. Containers 66 are filled with the substance and placed on a conveyer 68. Cover 65 with small opening 64 is used to minimize spillage and contamination of the substance. The conveyer moves intermittently and places each container 66 under device 69 for a set period of time. Device 69 is comprised of sealing element 70, which contains a number of openings, and cylinder 71. Cylinder 71 is formed to move sealing element 70 up and down from containers cover 65. Device 69 is formed to bring pressure pulsations from pressure pulsation generator 72 to the substance in containers 66. Any pressure pulsation generating device that has been described in the present invention can be employed in this application. The system operates in the following sequence: after container 66 is placed under sealing element 70, cylinder 71 extends and brings sealing element 70 in contact with cover 65 to seal opening 64; valves 67 and 65 shift to the "open" position and pump 25 starts pumping the product from tank 28 to pressurize the substance in container 66 before the pressure pulsation treatment begins; valve 67 shifts to a closed position and pressure pulsation generator 72 starts generating pressure pulsations to treat the substance in vessel 66; after the treatment, valve 65 closes and valve 67 opens, allowing double rotating pump 25 to suck back the excess product and prevent spillage; valve 67 closes again, sealing element 70 is lifted and vessel 66 is moved out of the way; the next in line vessel 66 is placed under device 69.

Figure 13:
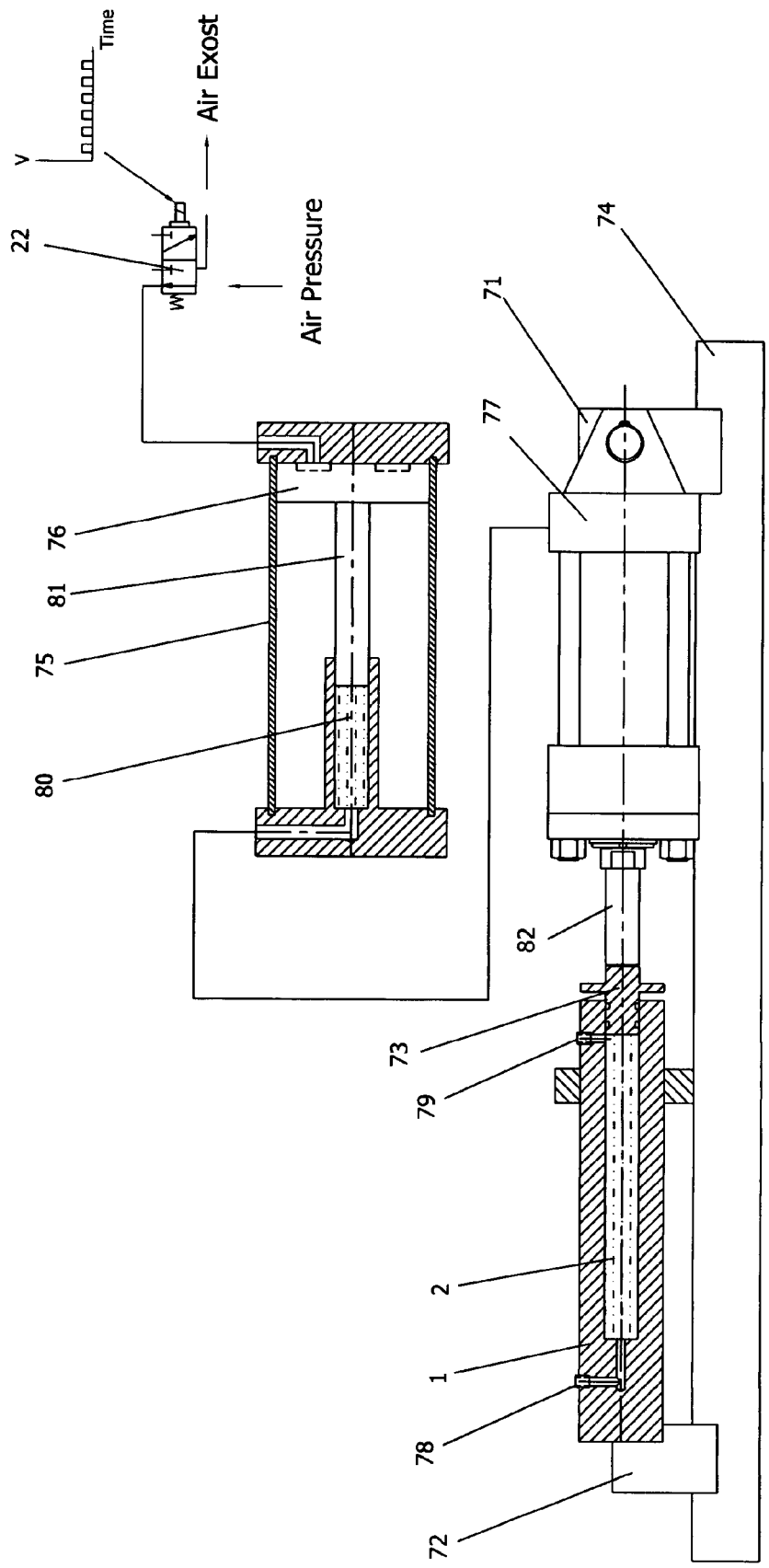
FIG. 13 is a cross-sectional view of present invention, where an air-hydraulic pressure buster and a hydraulic cylinder are used to produce high pressure pulsations in the liquid substance stored in the container.

With reference to FIG. 13, there is generally shown a cross sectional view of another system incorporating present invention. In this system, however, an air-hydraulic buster is incorporated to produce high pressure pulsations in treated substances. Vessel 1, containing product 2, and hydraulic cylinder 77 are shown in a horizontal position. Blocks 71 and 72 are mounted in pockets made in mounting plate 74 to support cylinder 77 and vessel 1 during operation. Plugs 78 and 79 are needed to close the openings in vessel 1 through which substance 2 can be loaded and unloaded. Air valve 22 brings air pressure to piston 76, which is placed inside air-hydraulic booster 75. Air valve 22 is controlled by an on-of pulsating signal. Through the action of piston rod 81 on the oil locked in cavity 80, low air pressure pulsations are transformed to high pressure hydraulic pulsations acting on cylinder 77. Since insignificant travel of piston rod 82 is required to generate pressure pulsations in substance 2, which is locked under pressure in vessel 1, a small air-hydraulic booster is sufficient to do the job. Air pressure is readily available in a laboratory or in industrial environment so this approach can provide a low cost and practical solution to generating high pressure pulsations with regulated frequency.

Figures 14, 14A:
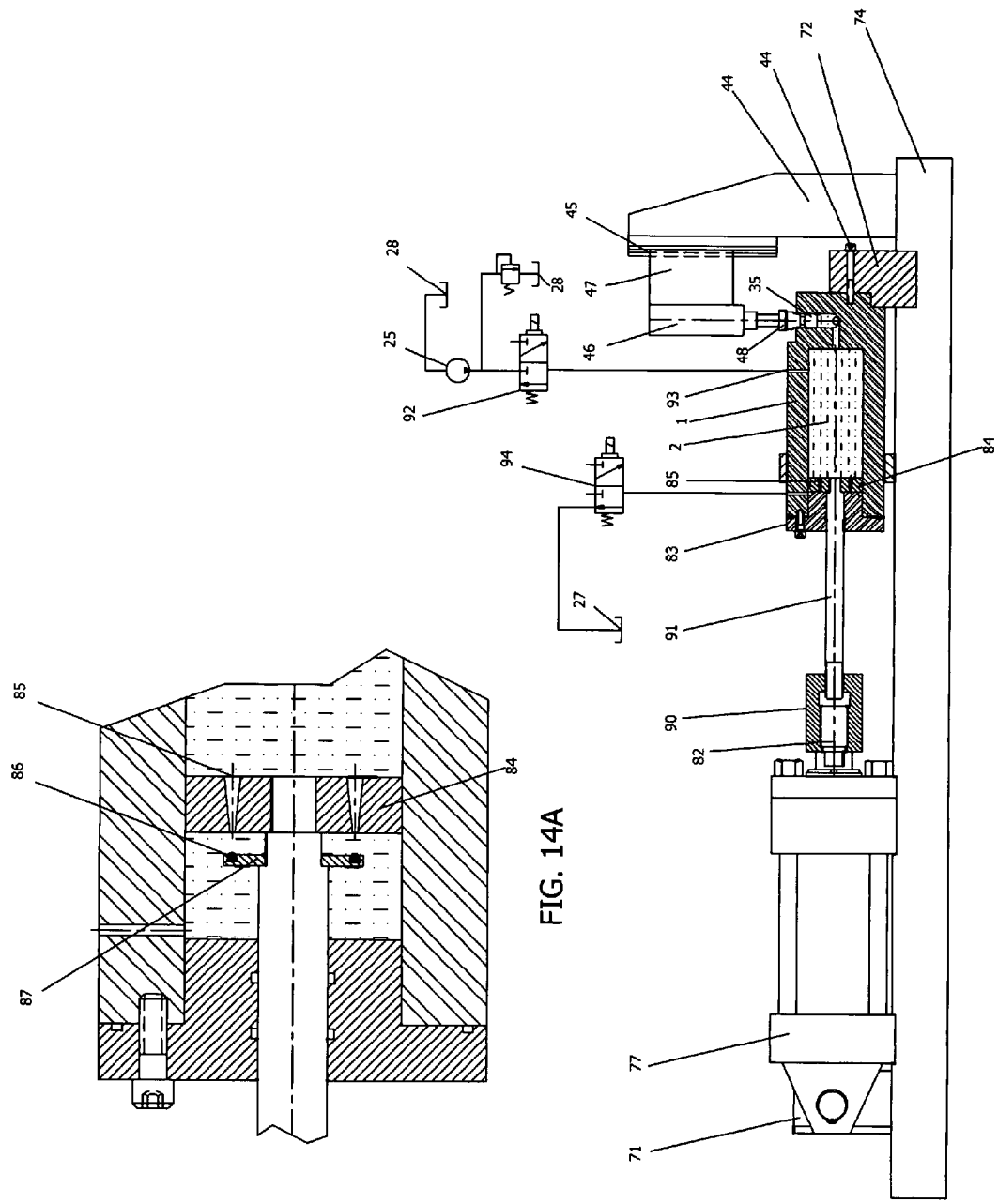
FIG. 14 is a cross-sectional view of present invention, where inactivation of harmful bacteria in a liquid substance and homogenization processes are combined in one apparatus comprising of a container with the pressure pulsation generating device and the homogenizing device formed on the opposite sides of the container.

With reference to FIG. 14 and FIG. 14A, there is generally shown a cross sectional view of another system incorporating present invention. In this system, however, two processes are involved in the treatment of liquid substances; homogenization and pressure pulsation with a set frequency are combined in the same vessel. Homogenization is a process used in the production of many foodstuffs. High pressure pulsations is this system are delivered by plunger 35. Delivering pressure pulsations to substance 2 in container 1 can be accomplished through plunger 35 by any of the devices described above. In the arrangement shown in FIG. 14, pressure pulsations are delivered by ultrasonic device 44 and vibrating horn 48. Homogenization of substance 2 is performed by cylinder 77. Piston rod 82 of cylinder 77 is attached to rod 91 through bushing 90. Rod 91, through an opening in closure 83 of vessel 1, is connected to piston 84, which is formed with small openings 85. Pump 25 fills vessel 1 with untreated substance from tank 28 through valve 92. Once vessel 1 is filled, valve 92 closes. At this point in the cycle, rod 82 is fully retracted. Piston 84 is pushed against sealing ring 86, which is retained in a groove of sliding ring 87, thus preventing the substance from escaping through openings 85. The process of killing bacteria in substance 2 begins when ultrasonic device 44 starts generating pressure pulsations in vessel 1. After the ultrasonic treatment is done, the homogenizing process begins. Piston rod 82 of cylinder 77 expands, pushing piston 84 through substance 2. Under the pressure in front of piston 84, retainer ring 87 is pushed back against the step formed on rod 91, thus allowing substance 2 to escape to the back of piston 84 through openings 85. When piston 84 reaches its far right position, valve 94 opens and rod 82 of cylinder 77 begins to retract. Retaining ring 87 with sealing ring 86 is being then pushed by inertia and pressure, against the back surface of piston 84, thus preventing substance 2 from escaping to the front of piston 84 through openings 85. Thereafter substance 2 moves to tank 27 through valve 94. The described system does not only allow the combination of pulsating pressure treatment and homogenization of the substance in one process, but also allows automatic unloading of the treated substance after treatment, which is another useful feature in mass production.

Figure 15:
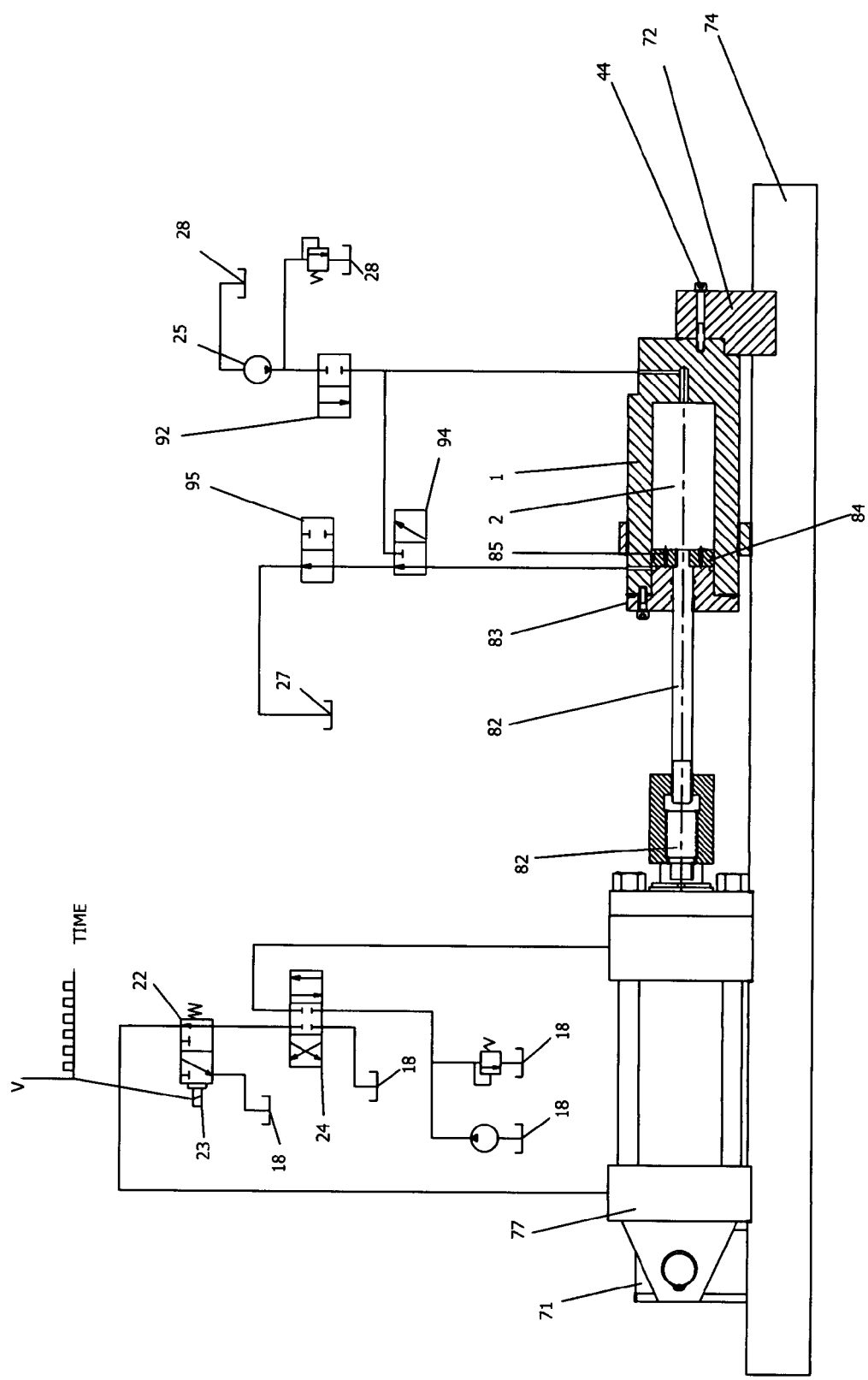
FIG. 15 is a cross-sectional view of present invention, where inactivation of harmful bacteria and homogenization processes are combined in one apparatus, in which both high pressure pulsation and homogenization treatment of the substance are done by one cylinder.

With reference to FIG. 15, there is generally shown a cross sectional view of another system incorporating present invention. In this system, however, high pressure pulsation and homogenization processes are combined and accomplished by one cylinder. Cylinder 77 is controlled by valves 22 and 24. This system works in the following sequence: as vessel 1 is filled with the untreated substance from storage tank 28 through valve 92 by pump 25, piston 84 is pushed to its extreme leftward position. When vessel 1 is filled with substance 2, under a pressure that is set by control valve 28, valves 92 and 95 close; valve 22 receives an "on" or "off" signal at a set frequency, generating pressure pulsations in cylinder 77, which are transferred to substance 2 in vessel 1. With each pressure pulsation, piston 84 moves a small distance to the right, forcing a small portion of substance 2 through openings 85 to the rear of piston 84, into the space that is formed by the rightward movement of piston 84. With this approach, the homogenization process is combined with the process of destruction of bacteria by high pressure pulsations. Valve 94 is utilized at the initial stage of the treatment process in order to equalize the duration of treatment of the substance located immediately in front of piston 84, with that of the substance located further away from piston 84, which spends more time in vessel 1 prior to efflux from the vessel. After piston 84 travels a set distance forward, valve 94 is shifted to its leftward position, piston rod 82 retracts, and the substance is returned from the space behind piston 84 to that in front of piston 84, where it undergoes additional pressure pulsation treatment. As soon as the initial equalization cycle is complete, valve 94 moves permanently to its rightward position, connecting the space behind piston 84 to valve 95, which is in its closed position. At this point, piston 84 starts to move rightward again, delivering pressure pulsations to substance 2. After it traverses some set distance (for example, one third of its total stroke), valve 95 opens, piston 84 is moved back to its starting position, and treated substance that had accumulated in the space behind piston 84 (as described above) is pushed into finished product tank 27. Meanwhile, untreated substance is added to vessel 1 from tank 28 through open valve 92 by pump 25, and the process resumes.

In the present invention, several different methods of generating the pulsating pressure for the purpose of immobilizing the undesired microorganisms in the liquid substances are described. These systems can also be fitted with interchangeable components, including different size actuators, cylinders and inserts, to provide a variety of pressure and frequency combinations. The variety of pressure and frequency combination is needed in conducting the research into the combination of the parameters that are most effective for use in production, that achieve the best results in the most economical and efficient way.

Various possible embodiments, forms and modifications of the invention, coming with the proper scope and spirit of the appended claims, will, of course, readily suggest themselves to those skilled in the art. Thus, while what has been described is at present considered to be preferred embodiments of the invention, it will be apparent to those skilled in the art that various changes and modifications can be made therein, without departing from the invention, and it is therefore the aim in the appended claims to cover all such changes and modifications as fall within the true spirit of the invention, and it is understood that, although the preferred form of the invention has been shown, various modifications can be made in the details thereof, without departing from the spirit as comprehended by the following claims.

What is claimed is:

1. Apparatus that induces instantaneous pressure pulsations in the liquid substances contained in a vessel for the purpose of destruction in the liquid substances of harmful microorganisms by applying to the liquid substances generated intermittent forces whose frequencies and amplitudes are regulated by independent controlling devices, said apparatus comprising:

A vessel that has one elongated opening;

A rod protruding from said opening that is formed to transmit to the liquid substances intermittent forces and is in contact with the liquid substances inside said opening and is tightly fitted with seals inside said opening to prevent the liquid substances contained inside said vessel from passing said rod;

A device that generates said intermittent forces;

A device that controls the frequency of the device that generates said intermittent forces; and A device that controls the amplitude of the device that generates said intermittent forces by controlling the pressure exerted on the device that generates said intermittent forces.

2. The apparatus of claim 1, wherein microorganisms are destroyed by frequencies that induce in said microorganisms a resonance condition.

3. The apparatus of claim 1, wherein the device that generates intermittent forces is a cylinder with a piston rod that intermittently strikes the liquid substances inside said elongated opening.

4. The apparatus of claim 1, wherein frequency of intermittent forces generated by the device is regulated by a rotary valve that rotates with controlled speed and intermittently switches pressure delivered to the device from low to high.

5. The apparatus of claim 1, wherein frequency of intermittent forces generated by the device is regulated by a solenoid valve that is controlled by intermittent on/off signal and switches pressure delivered to the device from low to high.

6. The apparatus of claim 1, wherein the device that generates intermittent forces is a rotating mechanical cam that intermittently strikes said rod and where the amplitude of an engagement force between said rod and the cam is regulated by an adjustable amortizing device.

7. The apparatus of claim 1, wherein the device that generates intermittent forces is a rotating wheel with a multitude of mechanical cams that are formed on its outer diameter and where the amplitude of an engagement force between said rod and said cams is regulated by an adjustable amortizing device.

8. The apparatus of claims 1, wherein pumps are used to automatically load, unload and pre-pressurize liquid substances.

9. The apparatus of claim 1, wherein said amplitudes of pressure pulsations in the liquid substances produced the same actuator are changed by the use of interchangeable inserts with sealed rods having different cross-sectional areas.

10. The apparatus of claim 1 further comprising, a second vibrating device that generates intermittent forces and where its vibrating member is intermittently separated from the sealed rod to strike said sealed rod with regulated frequencies including ultrasonic frequencies.

11. The apparatus of claim 1, wherein said vessel is formed with an opening for loading and unloading of solid products and where said opening is securely and tightly covered by a removable top constructed with a narrow vertical structure with an elongated opening retaining said rod.

12. The apparatus of claim 1, wherein cooling of the liquid substances is incorporated into the process of instantaneous pressure pulsation treatment.

13. The apparatus of claim 1, wherein an additional opening that is tightly closed for the duration of the pressure pulsation process is formed in the vessel or in its closure to facilitate removal of air trapped during loading of the liquid substances.

14. The apparatus of claim 1, wherein a second vessel with low inside pressure, a shut-off valve, and a restrictive nozzle are added to said apparatus, wherein the intermittent forces producing device is, in addition, programmed to periodically unload small portions of said substances, through said nozzle into the low pressure vessel.

15. The apparatus of claim 1, wherein the device that generates said intermittent forces is a gas-hydraulic booster that convert that converts gas pressure pulsations with low pressure amplitudes into hydraulic pressure pulsations with high hydraulic pressure amplitudes that intermittently strike said cylinders piston rod that is pushed against the liquid substances inside sealed elongated opening formed in said vessel.

16. The apparatus of claim 1, further comprising, a lid set up to move up and down, said lid comprising openings controlled by shut-off valves, wherein said lid is formed to be interchangeably coupled to a plurality of different pressure vessels to deliver instantaneous pressure pulsations to said one of said different pressure vessels when said one of said different pressure vessels is coupled with said lid.

17. The apparatus of claim 1, wherein the vessel is shaped as a cylinder having one sealed opening containing a sealed rod that is formed to transmit instantaneous pressure pulsations to the liquid substances and a second opening containing a sealed shaft attached to a plunger having a multitude of small openings and wherein said plunger is pushed forward and backward in accordance with the sequence of operation an independent device to combine the process of sterilization of the liquid substances contained in said vessel with the process of homogenization of said substances in the same vessel.

18. Apparatus for a process of destruction of harmful microorganisms in liquid substances contained in a vessel by induction in said substances instantaneous pressure pulsations, and a process of homogenization of said substances in said vessel, the apparatus comprising:

A cylindrically shaped vessel with openings for loading and unloading of said substances and an opening through which a sealed moveable rod is inserted;

An actuator that, in accordance with the sequence of operation, moves said moveable rod forward and backward along the vessel and generates intermittent forces, which induce instantaneous pressure pulsations in said substances;

A plunger attached to said rod, that is tightly fitted inside the cylindrically shaped vessel and has a multitude of small protruding openings;

A shut-off valve that is formed around moveable rod to automatically close protruding openings formed in said plunger to induce instantaneous pressure pulsations in said substances;

A device that controls frequency of intermittent forces produced by the actuator;
and
A device that controls amplitudes of intermittent forces produced by the actuator.

* * * * *